(12) United States Patent
Martin (10) Patent No.: US 8,105,967 B1
(45) Date of Patent: Jan. 31, 2012

(54) LIGHTWEIGHT BALLISTIC ARMOR INCLUDING NON-CERAMIC-INFILTRATED REACTION-BONDED-CERAMIC COMPOSITE MATERIAL

(75) Inventor: Curtis A. Martin, Damascus, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 408 days.

(21) Appl. No.: 12/286,285

(22) Filed: Sep. 26, 2008

Related U.S. Application Data (60) Provisional application No. 60/998,459, filed on Oct. 5, 2007.

(51) Int. Cl.
  *C04B 35/00* (2006.01)
  *B32B 3/26* (2006.01)
(52) U.S. Cl. .................... 501/97.4; 428/304.4
(58) Field of Classification Search .......... 501/97.1, 501/87, 96.1, 97.4; 428/304.4, 306.6, 307.3, 428/320.2; 89/36.01–36.17, 901–935
See application file for complete search history.

(56) References Cited

U.S. PATENT DOCUMENTS

| | | | | |
|---|---|---|---|---|
| 3,713,860 | A * | 1/1973 | Auskern .................. | 427/2.26 |
| 4,820,461 | A * | 4/1989 | Creber et al. ................ | 264/82 |
| 4,908,171 | A | 3/1990 | Claussen et al. | |
| 5,130,055 | A * | 7/1992 | Yasutomi et al. ............ | 252/516 |
| 5,135,691 | A * | 8/1992 | Hama et al. ................. | 264/624 |
| 5,141,748 | A | 8/1992 | Rizzo | |
| 5,158,916 | A | 10/1992 | Claussen | |
| 5,269,989 | A * | 12/1993 | Pyzik ......................... | 427/292 |
| 5,421,087 | A * | 6/1995 | Newkirk et al. ............. | 29/897.2 |
| 5,525,374 | A * | 6/1996 | Ritland et al. ............. | 427/376.1 |
| 5,843,859 | A | 12/1998 | Claussen | |
| 5,876,446 | A | 3/1999 | Agrawal et al. | |
| 5,947,893 | A | 9/1999 | Agrawal et al. | |
| 6,009,789 | A | 1/2000 | Lyons | |
| 6,025,065 | A | 2/2000 | Claussen et al. | |
| 6,051,277 | A | 4/2000 | Claussen et al. | |
| 6,228,933 | B1 | 5/2001 | Hiles | |
| 6,253,655 | B1 | 7/2001 | Lyons et al. | |
| 6,332,390 | B1 | 12/2001 | Lyons | |

(Continued)

OTHER PUBLICATIONS

Bhatt, 'Tensile Properties and Microstrucural Characterization of Hi-Nicalon SiC/RBSN composites', Oct. 1998, NASA/TM—1998-208657, CIMTEC '98, pp. 1-12.*

(Continued)

*Primary Examiner* — Jerry Lorengo
*Assistant Examiner* — Lynne Edmondson
(74) *Attorney, Agent, or Firm* — Howard Kaiser (57) ABSTRACT

According to typical inventive practice, precursor particulate is pressed and/or caste and/or molded and/or machined, thereby producing a porous green body of a desired shape. A gas is brought into contact with the porous green body so that, via reaction bonding between the gas and the porous green body, the porous green body becomes a porous reaction-bonded ceramic preform, geometrically corresponding to the porous green body. One or more infiltrant materials, at least one of which is glass or polymer, is/are caused to infiltrate the pores of the RB ceramic perform. The infiltrants are selected from glass, polymer, and metal. The infiltrated preform is permitted to cool and solidify, resulting in an embodiment of an inventive non-ceramic-infiltrated reaction-bonded-ceramic structure. Because of their potential material attributes such as strength, energy dissipation, and low density, the present invention's non-ceramic-infiltrated reaction-bonded-ceramic structures are especially favorable for inclusion in personal/personnel ballistic armor systems.

4 Claims, 5 Drawing Sheets

U.S. PATENT DOCUMENTS

| | | | |
|---|---|---|---|
| 6,532,857 | B1 | 3/2003 | Shih et al. |
| 6,573,210 | B1 | 6/2003 | Claussen et al. |
| 6,579,533 | B1 | 6/2003 | Tormala et al. |
| 6,601,497 | B2 | 8/2003 | Ghiorse et al. |
| 6,609,452 | B1 | 8/2003 | McCormick et al. |
| 6,737,493 | B2 | 5/2004 | Mochizuki et al. |
| 6,792,843 | B2 | 9/2004 | Mohr et al. |
| 6,804,829 | B2 | 10/2004 | Crye et al. |
| 6,860,186 | B2 | 3/2005 | Cohen |
| 6,892,392 | B2 | 5/2005 | Crye et al. |
| 6,972,130 | B1 | 12/2005 | Lee et al. |
| 7,026,045 | B2 * | 4/2006 | Rettenbacher et al. .... 428/306.6 |
| 7,067,031 | B2 | 6/2006 | deWitt |
| 7,080,587 | B2 | 7/2006 | Benyami et al. |
| 7,104,177 | B1 | 9/2006 | Aghajanian et al. |
| 7,114,764 | B1 | 10/2006 | Barsoum et al. |
| 7,128,963 | B2 | 10/2006 | Benitsch |
| 7,181,287 | B2 | 2/2007 | Greenberg |
| 7,210,390 | B1 | 5/2007 | Olson et al. |
| 7,237,270 | B2 | 7/2007 | Crye et al. |
| 7,267,882 | B2 | 9/2007 | Breslin et al. |
| 7,284,469 | B2 | 10/2007 | Raichel et al. |
| 7,294,409 | B2 | 11/2007 | Lye et al. |
| 7,300,893 | B2 | 11/2007 | Barsoum et al. |
| 7,332,221 | B2 | 2/2008 | Aghajanian et al. |
| D569,043 | S | 5/2008 | Crye et al. |
| D569,044 | S | 5/2008 | Crye et al. |
| D569,045 | S | 5/2008 | Crye et al. |
| D569,046 | S | 5/2008 | Crye et al. |
| 7,383,762 | B2 | 6/2008 | Cohen |
| D573,311 | S | 7/2008 | Crye et al. |
| 7,419,681 | B2 | 9/2008 | Tormala et al. |
| 2001/0037659 | A1 * | 11/2001 | Sakai et al. .................... 65/17.2 |
| 2004/0197542 | A1 * | 10/2004 | Benitsch .................... 428/304.4 |
| 2007/0093158 | A1 | 4/2007 | Dudt et al. |
| 2007/0111621 | A1 | 5/2007 | Barsoum et al. |

OTHER PUBLICATIONS

U.S. Appl. No. 60/998,459, filed Oct. 5, 2007, invention title "Ballistic Armor Methods, Systems and Materials," joint inventors Curtis A. Martin, Gilbert F. Lee, Jeffrey J. Fedderly, David E. Johnson, David P. Owen, Rodney O. Peterson, Philip J. Dudt, James A. Zaykoski, and Inna G. Talmy.

U.S. Appl. No. 60/564,584, filed Apr. 23, 2004, entitled "Armor Including a Strain Rate Hardening Elastomer," joint inventors Roshdy George S. Barsoum, and Philip Dudt.

Co-pending U.S. Appl. No. 11/973,990, filed Oct. 5, 2007, entitled "Composite Ballistic Armor Having Geometric Ceramic Elements for Shock Wave Attenuation," joint inventors Curtis A. Martin, Gilbert F. Lee, and Jeffrey J. Fedderly.

Co-pending U.S. Appl. No. 11/973,999, filed Oct. 5, 2007, entitled "Ballistic Armor Methodology Using Low-Density Ceramic Material," joint inventors Curtis A. Martin, David E. Johnson, David P. Owen, Rodney O. Peterson, and Philip J. Dudt.

Malcolm E. Washburn and William S. Coblenz, "Reaction-Formed Ceramics," *Ceramic Bulletin*, American Ceramic Society (ACerS), vol. 67, No. 2, pp. 356-357 and 360-363.

Rolf Janssen, Sven Scheppokat, Nils Claussen, "Tailor-Made Ceramic-Based Components—Advantages by Reactive Processing and Advanced Shaping Techniques," *Journal of the European Ceramic Society*, vol. 28, pp. 1369-1379 (available online Feb. 14, 2008).

Nils Claussen et al., "Squeeze Cast $\beta$-$Si_3N_4$-Al Composites," *Advanced Engineering Materials*, vol. 4, No. 3, pp. 117-119 (published online Mar. 12, 2002).

N. A. Travitzky and N. Claussen, "Microstructure and Properties of Metal Infiltrated RBSN Composites," *Journal Of The European Ceramics Society*, vol. 9, No. 1, pp. 61-65 (1992).

* cited by examiner

LIGHTWEIGHT BALLISTIC ARMOR INCLUDING NON-CERAMIC-INFILTRATED REACTION-BONDED-CERAMIC COMPOSITE MATERIAL

CROSS-REFERENCE TO RELATED APPLICATIONS

This application claims the benefit of U.S. provisional patent application No. 60/998,459, hereby incorporated herein by reference, filing date 5 Oct. 2007, invention title "Ballistic Armor Methods, Systems and Materials," joint inventors Curtis A. Martin, Gilbert F. Lee, Jeffrey J. Fedderly, David E. Johnson, David P. Owen, Rodney O. Peterson, Philip J. Dudt, James A. Zaykoski, Irma G. Talmy.

BACKGROUND OF THE INVENTION

The present invention relates to material compositions that include ceramic material, and to methods, systems, devices, and articles involving such compositions, more particularly such compositions that are relatively low in density and are otherwise suitable for use in personnel/personal ballistic armor applications.

Current military armor applications include manned land vehicles, manned air vehicles (e.g., aircraft and rotorcraft), stationary structures, and persons. Other applications of armor systems are less common but may become more prevalent in the future, including unmanned air vehicles, manned marine vehicles (e.g., ships), unmanned marine vehicles, and missiles.

Various armor constructions and configurations have been disclosed involving utilization of ceramic material. See, e.g., the following U.S. patents, each of which is incorporated herein by reference: Cohen, U.S. Pat. No. 7,383,762 B2, issued 10 Jun. 2008, entitled "Ceramic Pellets and Composite Armor Panel Containing the Same"; Aghajanian et al., U.S. Pat. No. 7,332,221 B2, issued 12 Sep. 2008, entitled "Boron Carbide Composite Bodies, and Methods for Making Same"; Raichel et al., U.S. Pat. No. 7,284,469 B2, issued 23 Oct. 2007, entitled "Protection from Kinetic Threats Using Glass-Ceramic Material"; Breslin et al., U.S. Pat. No. 7,267,882 B2, issued 11 Sep. 2007, entitled "Ceramic/Metal Material and Method for Making Same"; Benitsch U.S. Pat. No. 7,128,963 B2, issued 31 Oct. 2006, entitled "Ceramic Composite Body, Method for Fabricating Ceramic Composite Bodies, and Armor Using Ceramic Composite Bodies"; Aghajanian et al. U.S. Pat. No. 7,104,177 B1 issued 12 Sep. 2006, entitled "Ceramic-Rich Composite Armor, and Methods for Making Same"; deWitt, U.S. Pat. No. 7,067,031 B2, issued 27 Jun. 2006, entitled "Process for Making A Ceramic Armor Plate"; Rettenbacher et al., U.S. Pat. No. 7,026,045 B2, issued 11 Apr. 2006, entitled "Multilayer Composite Armour"; Cohen, U.S. Pat. No. 6,860,186 B2, issued 1 Mar. 2005, entitled "Ceramic Bodies and Ballistic Armor Incorporating the Same"; Mohr et al., U.S. Pat. No. 6,792,843 B2, issued 21 Sep. 2004, entitled "Armor-Plating Composite"; McCormick et al., U.S. Pat. No. 6,609,452 B1, issued 26 Aug. 2003, entitled "Silicon Carbide Armor Bodies, and Methods for Making Same"; Ghiorse et al., U.S. Pat. No. 6,601,497 B2, issued 5 Aug. 2003, entitled "Armor with In-Plane Confinement of Ceramic Tiles"; Shih et al., U.S. Pat. No. 6,532,857 B1, issued 18 Mar. 2003, entitled "Ceramic Array Armor"; Lyons, U.S. Pat. No. 6,332,390 B1, issued 25 Dec. 2001, entitled "Ceramic Tile Armor with Enhanced Joint and Edge Protection"; Lyons et al., U.S. Pat. No. 6,253,655 B1, issued 3 Jul. 2001, entitled "Lightweight Armor with a Durable Spall Cover"; Lyons, U.S. Pat. No. 6,009,789, issued 4 Jan. 2000, entitled "Ceramic Tile Armor with Enhanced Joint and Edge Protection."

Ceramic materials that are particularly known in the art to be suitable for use in armor applications include aluminum oxide (commonly called "alumina"), silicon carbide, boron carbide, and titanium carbide. These conventional armor ceramics have been developed over the last thirty years or so, represent the current state of the art, and have been relied upon in conventional practice of armor systems—for instance, for protection against impact by a projectile such as a ballistic body (e.g., small arms fire) or an explosive fragment (e.g., shrapnel from a bomb blast). Although conventional ceramic armor materials often perform satisfactorily, they (and therefore armor systems implementing them) tend to be expensive to produce. Furthermore, conventional ceramic armor materials sometimes fail, or perform less than optimally, when impacted by a projectile. Generally speaking, there is a recognized and continuing need in the armor-related arts to improve the capabilities of materials to withstand significant impacts.

The weight of an armor system tends to be more critical in the realm of personnel/personal armor, such as helmets and body armor. Through the years, military helmets have evolved from the metal (e.g., steel) helmets of the First and Second World Wars, to plastic helmets, to the current state-of-the-art composite helmets. U.S. ground troops are currently outfitted with a polymer composite helmet including aramid fibers that is capable of stopping handgun threats but is incapable of stopping greater projectile threats, such as rifles and other more powerful firearms. Body armor members (e.g., plates) made of ceramic, metal (e.g., steel or titanium), or polyethylene have seen development for use by military and law enforcement. In particular, body armor systems employing one or more ceramic inserts have recently seen military use, and have demonstrated varying degrees of imperviousness to greater projectile threats, but these body armor systems have been criticized for imposing excessive weight upon the wearer. In addition, modern-day personnel/personal armor systems have generally been expensive to mass-produce.

In theory, a ballistic helmet or vest made of a ceramic material could provide greater resistance to projectile impact than what is currently used. In practice, however, items such as helmets and vests represent especially difficult applications for ceramic armor because of both weight restrictions and specialized shapes. Ceramic armor materials of more advanced capabilities are most often prepared by hot-pressing (pressure-assisted sintering), a technique that is not suitable for preparation of an article of complex shape, such as a helmet or a vest; in general, hot-pressing is limited in terms of reduced production capacity and higher production cost.

Accordingly, in the realm of personnel/personal armor, the need exists for materials and systems that are practical and economical for extensive manufacture, are sufficiently lightweight, and afford more effective ballistic protection than current versions.

SUMMARY OF THE INVENTION

In view of the foregoing, an object of the present invention is to provide a new personnel/personal ballistic armor system that, as compared with conventional personnel/personal ballistic armor systems, affords superior performance in terms of imperviousness to projectile impact.

Another object of the present invention is to provide a new personnel/personal ballistic body-armor system that, as compared with conventional personnel/personal ballistic armor systems, is lighter in weight.

A further object of the present invention is to provide a new personnel/personal ballistic body-armor system that, as compared with conventional personnel/personal ballistic armor systems, can be cost-effectively produced on larger scales.

In accordance with typical practice of the present invention, an inventive composite structure comprises a reaction-bonded ceramic preform and a non-ceramic infiltrant. The non-ceramic infiltrant is either glass or polymer. The reaction-bonded ceramic preform is characterized by porosity in the approximate range between ten percent and sixty percent of its volume. The non-ceramic infiltrant at least substantially fills the porosity of the reaction-bonded ceramic preform.

According to frequent inventive practice, an inventive composite structure comprises a reaction-bonded ceramic preform and at least two different non-ceramic infiltrants. Each non-ceramic infiltrant is either glass or polymer or metal. At least one non-ceramic infiltrant is either glass or polymer. The reaction-bonded ceramic perform is characterized by porosity in the approximate range between ten percent and sixty percent of its volume. Each non-ceramic infiltrant fills at least one portion of the porosity of the reaction-bonded ceramic perform. The at least two non-ceramic infiltrants at least substantially fill the porosity of the reaction-bonded ceramic preform.

Some embodiments of inventive structures, such as the inventive composite structure described herein in the preceding paragraph, are characterized by plural infiltrants. A typical inventive method for making a composite structure comprises: (a) forming a porous green body from unformed precursor material; (b) converting the porous green body to a porous reaction-bonded ceramic perform; (c) infiltrating the porous reaction-bonded ceramic perform with at least two different non-ceramic infiltrants. Each non-ceramic infiltrant is either glass or polymer or metal. At least one non-ceramic infiltrant is either glass or polymer. The converting to a porous reaction-bonded ceramic perform includes associating a gaseous substance with the porous green body. The porous reaction-bonded ceramic preform is characterized by porosity in the approximate range between ten percent and sixty percent of its volume. The infiltrating is performed so that each non-ceramic infiltrant permeates at least one portion of the porosity, and so that the at least two non-ceramic infiltrants at least substantially permeate the porosity.

The present invention's lightweight composite materials, as typically embodied, are synonymously referred to herein as "non-ceramic-infiltrated reaction-bonded ceramic preforms," or "non-ceramic-infiltrated reaction-bonded-ceramic-preform composites," or "non-ceramic-infiltrated reaction-bonded-ceramic-preform composite materials," or "non-ceramic-infiltrated reaction-bonded-ceramic composites," or "non-ceramic-infiltrated reaction-bonded-ceramic composite materials." The inventive composite materials, and methods of making same, are particularly suitable for ballistic armor applications. Typical inventive practice features the infiltration of a metallic material and/or a polymeric material and/or a glass material into a reaction-bonded porous ceramic, such as a reaction-bonded silicon nitride ("RBSN"). Of particular note, previously unknown are the present invention's RBSN-glass composites, RBSN-polymer composites, RBSN-glass-polymer composites, RBSN-metal-polymer composites, RBSN-metal-glass composites, and RBSN-metal-polymer-glass composites.

Inventive practice frequently provides for the infiltration of a non-ceramic infiltrant (infiltrator) material into a reaction-bonded ceramic preform in order to make a personnel/personal ballistic armor article or device. A reaction-bonded ceramic preform is infiltrated with metal, polymer (e.g., elastomer), and/or glass so as to produce a personnel/personal ballistic armor article or device of a desired complex shape (such as a helmet shape or a vest shape) or a desired simple shape (such as a tile/plate shape). Inventive composites consisting essentially of reaction-bonded ceramic preform and metal, ceramic, and/or polymer infiltrant(s) are especially suitable for lightweight armor applications in which armor weight is critical but the need exists to increase the level of protection to cover more "aggressive" fragments, bullets, or other projectiles.

The term "ceramic-inclusive material" is used herein to denote any material that includes at least one ceramic material. For instance, a ceramic-inclusive material that consists of a single ceramic material is referred to herein as a "pure ceramic material" or a "pure ceramic," or simply as a "ceramic material" or "ceramic." The afore-noted conventional ceramic armor materials (aluminum oxide, silicon carbide, boron carbide, titanium carbide, etc.) represent pure ceramic materials. A ceramic-inclusive material that consists of at least two ceramic materials is synonymously referred to herein as a "ceramic-ceramic composite material" or "composite ceramic-ceramic material" or "ceramic-ceramic composite." A ceramic-inclusive material that consists of at least one ceramic material and at least one non-ceramic material is synonymously referred to herein as a "ceramic-non-ceramic composite material" or "composite ceramic-non-ceramic material" or "ceramic-non-ceramic composite." The inventive non-ceramic-infiltrated reaction-bonded ceramic preform composite materials represent "ceramic-non-ceramic" composite materials.

Conventional ceramic armor materials do not lend themselves to preparation in complex shapes. In contrast, according to many embodiments of the present invention, a reaction-bonded "pure" ceramic material such as reaction-bonded silicon nitride (RBSN) is prepared rather easily in a complex shape such as a helmet shape or vest shape. The specially shaped reaction-bonded ceramic (e.g., RBSN) preform is then readily infiltrated with at least one non-ceramic infiltrant material selected from among one or more of three categories of non-ceramic infiltrant material, viz., (i) metal, (ii) polymer (e.g., elastomer), and (iii) glass. The present invention's resultant personnel/personal ballistic armor article/device is a specifically configured "ceramic-non-ceramic" composite.

The term "metal," as used herein in context of inventive practice, refers to any metallic material, whether elemental metal or metal alloy. The term glass, as used herein, denotes "glass" in its broadest conventional sense. Glass is conventionally understood to mean any material made by cooling molten material in such a manner that it fails to crystallize and remains in an amorphous state. The material's viscosity increases to such a high value that, as a practical matter, the material is solid. Most commercial glasses are silicates, i.e., include silica ($SiO_2$). Notable properties of glass include viscosity and light transmission. The term "polymer," as used herein, refers to any polymeric material in the broadest conventional sense, including thermoplastic polymers and thermosetting polymers. Examples of polymeric materials that may be suitable for inventive practice, depending on the inventive embodiment, include but are not limited to polyurethane, polyurea, polyethylene, neoprene, acrylic, etc., or any combinations of two or more individual polymers.

Inventive practice holds interesting possibilities for ballistic armor applications in terms of diverse ingredients, types, and shapes of composites that combine ceramic materials with metal materials and/or glass materials and/or polymeric (e.g., elastomeric) materials. Advantageously, the present invention's ceramic-non-ceramic composite as typically embodied exhibits reduced density, and therefore reduced weight, because it is constituted as if part of the ceramic material has been replaced with less dense material; in effect, a metal material (especially, a light metal such as aluminum) and/or a polymeric material (e.g., elastomer) and/or a glass material has/have been substituted for a portion or portions of the total volume of the ceramic material. For instance, let us assume that the porosity of an RBSN body is filled with a light metal, or a glass, or a polymer, or some combination thereof, in accordance with the present invention; the RBSN body thus inventively rendered "pore-free" via infiltration will have a somewhat lower overall density than will a fully dense silicon nitride body, and will have a significantly lower overall density than will a fully dense alumina body.

Techniques are known for making various kinds of ceramic-metal composites. A first known methodology for creating a ceramic-metal composite involves the combination of ceramic powder with a metal component through dispersion of ceramic powder into the melted metal component. A second known methodology for preparing a ceramic-metal composite involves the partial sintering of ceramic material to obtain a porous ceramic preform, followed by pressureless or pressure-assisted melt infiltration of the porous partially sintered ceramic preform with a metal. Of particular interest herein is a third known methodology for preparing a ceramic-metal composite, which involves the reaction-bonding of two non-ceramic substances to obtain a porous ceramic preform, followed by pressureless or pressure-assisted melt infiltration of the porous reaction-bonded ceramic preform with a metal. The present invention incorporates principles of this third known methodology insofar as involving infiltration of a non-ceramic material into a porous reaction-bonded ceramic preform.

Other objects, advantages and features of the present invention will become apparent from the following detailed description of the present invention when considered in conjunction with the accompanying drawings.

BRIEF DESCRIPTION OF THE DRAWINGS

The present invention will now be described, by way of example, with reference to the accompanying drawings, wherein like numbers indicate same or similar parts or components, and wherein:

FIG. 10 is a schematic, similar to FIG. 1, of an embodiment of an inventive method for making a plural-infiltrant embodiment of an inventive composite device or article. In particular, FIG. 10 illustrates an inventive "porosity-gradient" technique, which can be practiced in inventively fabricating an inventive plural-infiltrant embodiment.

DESCRIPTION OF EXEMPLARY
EMBODIMENTS OF THE INVENTION

As previously noted herein, a variety of reaction-bonded ceramic materials may be suitable for practicing the present invention. Although the examples hereinbelow of inventive practice specifically involve RBSN as the ceramic preform material, it is reemphasized that any ceramic may be inventively suitable that is capable of being formed by reaction-bonding of a substance with a powder precursor.

Moreover, although the examples hereinbelow of inventive practice are especially descriptive of body armor plates (such as would be suitable for inclusion in ballistic body armor systems) and fabrication thereof, it is to be understood that the present invention admits of practice in multifarious other applications, including but not limited to: other personnel/personal ballistic armor applications, such as helmets; non-personnel/personal ballistic armor applications, such as for vehicles and stationary structures; sports applications, such as for protecting football players, hockey players and referees, baseball players and umpires, bicyclists, and racecar drivers; mechanical applications, such as for promoting wear reduction of bearings and other mechanical parts/components; medical applications, such as for effecting or facilitating drug delivery or bone ingrowth; decorative/aesthetic applications, such as statues and other ornamental articles.

The drawings herein are not intended to be realistic but rather diagrammatic in nature. For instance, for illustrative purposes the pores are represented as discrete circles, rather than more accurately portrayed in terms of their non-uniform, interconnected, irregular and interstitial sizes, shapes and configurations. In a similar vein, the drawings are not intended to be suggestive, for instance, of inventive practical preference with regard to the volume fraction of the pores or of the RB ceramic containing them.

Figure 1:
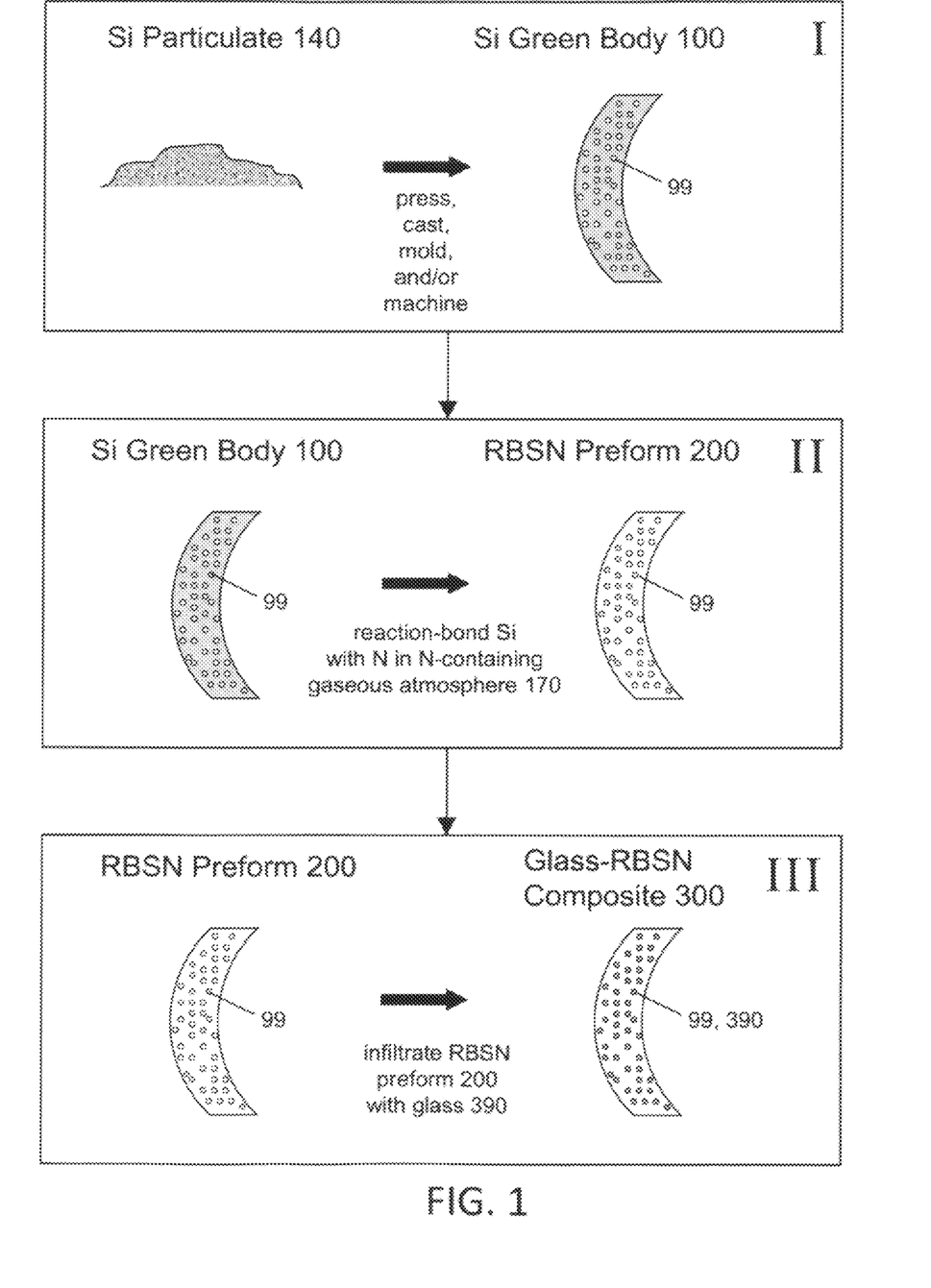
FIG. 1 is a schematic of typical practice, in accordance with the present invention, of making an inventive composite device or article, such as an inventive body armor plate.

Referring now to FIG. 1, a typical inventive method for making an inventive non-ceramic-infiltrated RBSN-preform composite includes three stages, as follows: (1) forming a porous silicon green body 100 (characterized by pores 99) from unformed silicon material (e.g., silicon powder) 140; (2) associating a nitrogen-inclusive gas 170 with the porous silicon green body 100, thereby converting the porous silicon green body 100 to a porous RBSN ceramic preform 200 (characterized by pores 99 and composed of RBSN ceramic material 210) via bondingly reactive interaction between the gaseous-state nitrogen 170 and the solid-state silicon 140; (3) infiltrating the porous RBSN ceramic preform 200 with one or more non-ceramic material infiltrants 390, thereby producing a non-ceramic-infiltrated RBSN composite 300 having an RBSN ceramic material phase 210 (composed of RBSN ceramic material 210 and corresponding to RBSN ceramic preform 200) and a non-ceramic material phase 390 (composed of non-ceramic material infiltrant/infiltrants 390 and at least substantially filling the vacant pores 99 of RBSN ceramic preform 200).

In accordance with typical inventive practice involving reaction-bonded silicon nitride (RBSN), the first main step is to form a "green body" 100 of silicon particles 140 (e.g., by pressing, casting, or molding). This formation of a green body 100 of a desired shape paves the way for subsequent formation, using the green body 100, of an RBSN preform 200 having (essentially) the same shape but a different (i.e., ceramic) composition. The porous silicon green body 100 is prepared by pressing the reactive powder 140, viz., silicon powder, into shape. The shaping of a quantity of silicon powder to form a green body can be accomplished via one or more conventional pressureless or pressure-assisted shaping techniques, such as die pressing, cold isostatic pressing, slip casting, and/or injection molding. In addition, if required, machining of the green body thus produced can be performed to refine its shape.

According to the second main step as illustrated in FIG. 1, the porous silicon green body 100 is converted to a porous silicon nitride ceramic preform 200 by firing the porous silicon green body 100 in an atmosphere of nitrogen-inclusive gas 170. The green body 100 is reacted with a nitrogen-inclusive gas (e.g., a pure nitrogen gas or a nitrogen-bearing gas such as ammonia) 170, resulting in conversion of the green body 100's silicon particles 140 to the ceramic preform 200's silicon nitride grains 210. The reaction-bonding of the nitrogen with the silicon will not significantly affect the basic structure of the silicon green body 100, and thus the structure (including porosity) of the RBSN body/preform 200 will be at least substantially congruous with the structure (including porosity) of the silicon green body 100. The silicon green body 100, and hence the reaction-bonded silicon nitride body/preform 200 that is derived from it, is necessarily porous. Otherwise expressed, the silicon green body 100, and hence the reaction-bonded silicon nitride body/preform 200, can never be pore-free (i.e., fully dense).

An important aspect of typical inventive practice is selection of the porosity (and therefore the density) of the reaction-bonded ceramic body/preform 200, through control of the "green density" (i.e., the density of the green body 100). For instance, the inventive practitioner can dictate the porosity (and therefore the density) of an RBSN body/preform 200 by regulating the density of the Si green body 100. As elaborated upon hereinbelow, according to some embodiments of inventive fabrication methodology of a heterogeneously infiltrated reaction-bonded ceramic, the green body production phase can be effected so as to create a geometric gradient, particularly in terms of pore size, in the green body's pore structure.

It is pointed out that, generally speaking, the porosity of the RB ceramic preform 200 will not exactly match the porosity of the green body 100 from whence it comes. Usually, the respective porosities of the RB ceramic perform 200 and the green body 100 will be close, comparable or analogous, but not identical. The RB ceramic preform 200's porosity will tend to be less than the green body 100's porosity. For instance, when Si particles convert to silicon nitride, there is a volume increase, resulting in a porosity decrease due to constant overall compact volume; therefore, the silicon nitride preform body is less porous than the silicon green body.

Reaction-bonded silicon nitride ($Si_3N_4$), commonly designated "RBSN," is a noteworthy ceramic preform material for inventive practice. RBSN is believed by the present inventor to be an especially promising preform material for armor applications. Generally, the silicon nitride grains in RBSN are interlocked and well-bonded; in fact, the bonding between the grains in RBSN is generally stronger than that of partially sintered ceramics. Based on the varying strengths for varying porosities of RBSN as reported by the below-noted Claussen et al., "Squeeze Cast $\beta$-$Si_3N_4$—Al Composites," the flexural strength of porous RBSN with more than 40% porosity can be over 250 Mpa, which is almost as strong as fully dense 90% alumina, a common armor material.

Other reaction-bonded ceramic materials may also be suitable or propitious for constituting the preform 200 to be infiltrated according to inventive practice, including but not limited to reaction-bonded silicon carbide (RBSC), reaction-bonded titanium carbide (RBTC), reaction-bonded titanium oxide (RBTO), and reaction-bonded aluminum oxide (RBAO). Among these RB ceramics, at least, RBSN is believed by the present inventor to have the highest strength, modulus, and ballistic properties. Any ceramic that can be formed by reaction from a powder precursor can be used to form a reaction-bonded ceramic in accordance with the present invention. Reaction-bonding of a precursor to form a reaction-bonded ceramic is typically effected by associating a solid particulate precursor with a gaseous substance; nevertheless, depending on the precursor material and the material with which the precursor reaction-bonds, the latter material can be selected to exist for the reaction-bonding process in any physical state, e.g., solid, liquid, or gas.

If a non-nitride RB ceramic preform material is being made, an appropriate gaseous atmosphere other than nitrogen may be used for firing the porous green body 100. For instance, a porous silicon green body 100 is converted to silicon carbide ceramic 200 by firing the porous silicon green body 100 in a carbonaceous atmosphere; a porous titanium green body 100 is converted to titanium carbide ceramic 200 by firing the porous silicon green body 100 in a carbonaceous atmosphere; a porous titanium green body 100 is converted to titanium oxide ceramic 200 by firing the porous titanium green body 100 in an oxygen atmosphere; a porous aluminum green body 100 is converted to aluminum oxide ceramic 200 by firing the porous aluminum green body 100 in an oxygen atmosphere. Known in the industry are the firing temperatures and the firing rates that are specific to the starting powder (e.g., silicon, titanium, or aluminum), the gas (e.g., nitrogen, carbon, or oxygen), and the RB ceramic 200 being formed (e.g., RBSN, RBSC, RBTC, RBTO, or RBTC).

Note that an RB ceramic such as reaction-bonded silicon carbide (RBSC) differs from an RB ceramic such as reaction-bonded silicon nitride (RBSN). To make an RBSC body, the silicon green body is caused to react with carbon to make a solid silicon carbide phase. Although the resultant reaction-bonded SiC material is predominantly ceramic, it may have some residual silicon metal at grain boundaries; see, e.g., the aforementioned McCormick et al., U.S. Pat. No. 6,609,452 B1.

After conversion of the porous Si green body 100 to an RBSN preform 200, machining (or further machining, if machining was previously performed of the Si green body) can be performed, for shape refinement purposes, of the reaction-bonded silicon nitride preform 200. As a general observation, the relative ease with which RBSN material can be formed in diverse complex shapes is evidenced by the current commercial manufacture of vehicular and other technical parts and components (automotive turbocharger rotors, jet engine components, etc.), such as manufactured by Ceradyne, Inc., 3169 Redhill Avenue, Costa Mesa, Calif., 92626, http://www.ceradyne.com.

Various reaction-bonded ceramic materials are known in the ceramic arts. See, e.g., Malcolm E. Washburn and William S. Coblenz, "Reaction-Formed Ceramics," *Ceramic Bulletin*, American Ceramic Society (ACerS), Volume 67, Number 2, pages 356-363, incorporated herein by reference; Rolf Janssen, Sven Scheppokat, Nils Claussen, "Tailor-Made Ceramic-Based Components—Advantages by Reactive Processing and Advanced Shaping Techniques," *Journal of the European Ceramic Society*, Volume 28, pages 1369-1379 (available online 14 Feb. 2008), incorporated herein by reference.

Still with reference to FIG. 1, the third main step of the present invention's fabrication method, as typically embodied, is to infiltrate the reaction-bonded silicon nitride (RBSN) preform 200 with at least one non-ceramic infiltrant material 390 that is in molten form. The non-ceramic-infiltrated RB preform is permitted to cool so that the moltenly applied infiltrant solidifies. The result is an integral composite structure 300 characterized by a porous ceramic matrix material 210 and one or more non-ceramic filler materials 390 that at least substantially occupy the pores 99 described by the ceramic matrix material.

The present invention provides for utilization/effectuation of either a single infiltrant or plural infiltrants in association with a given RB ceramic preform, depending on the inventive embodiment, and the terms "homogenous" and "heterogeneous" are correspondingly used herein. Inventive infiltration of an RB ceramic preform can be either homogenous (wherein a single non-ceramic material is infiltrated into the RB ceramic preform) or heterogeneous (wherein two or more different non-ceramic materials are infiltrated into the RB ceramic preform).

A typical inventive homogeneously infiltrated RB ceramic preform is an RB ceramic preform that is completely or substantially filled with one non-ceramic material. A typical inventive heterogeneously infiltrated RB ceramic preform is an RB ceramic preform that is completely or substantially filled with two or more non-ceramic materials in such a manner that the individual ceramic materials are macroscopically distinct from each other. The present invention's non-ceramic-infiltrated RB-ceramic-preform composite, whether of the homogeneously infiltrated variety or the heterogeneously infiltrated variety, can be embodied so as to be "supersaturatedly" filled (filled to excess) with one or more infiltrants so that one or more infiltrants, when hardened, constitute(s) an outside layer (e.g., coating or glaze).

A typical inventive non-ceramic-infiltrated reaction-bonded-ceramic composite material is characterized by relatively low density. The low density of the inventive non-ceramic-infiltrated RB ceramic preform is associated with the low density of the silicon green body, and hence of the RB ceramic preform, as the porosity of the RB ceramic preform is the same or substantially the same as the porosity of the silicon green body. As a general rule, the porosity of an inventive reaction-bonded ceramic preform can have a value in the range between approximately ten percent porosity by volume to approximately sixty percent porosity by volume. The porosity can be as high as can be reasonably achieved to maintain good strength (e.g., about 60% porosity), and can be as low as can be reasonably achieved to maintain open continuous porosity (e.g., about 10% porosity). The higher the porosity of the RB ceramic preform, the lower its density.

As noted hereinabove, the present invention to some extent avails itself of a previously disclosed methodology for infiltrating a metallic material into a porous reaction-bonded silicon nitride ceramic preform. The following two references, each of which is incorporated herein by reference, disclose RBSN-metal composites: Nils Claussen et al., "Squeeze Cast $\beta$-$Si_3N_4$—Al Composites," *Advanced Engineering Materials*, volume 4, number 3, pages 117-119 (2002); N. A. Travitzky and N. Claussen, "Microstructure and Properties of Metal Infiltrated RBSN Composites," *Journal Of The European Ceramics Society*, volume 9, number 1, pages 61-65 (1992). See also the following United States patent documents, each of which is incorporated herein by reference: Claussen et al. U.S. Pat. No. 6,573,210 B1 issued 3 Jun. 2003; Claussen et al. U.S. Pat. No. 6,051,277 issued 18 Apr. 2000; Claussen et al. U.S. Pat. No. 6,025,065 issued 15 Feb. 2000; Claussen U.S. Pat. No. 5,843,859 issued 1 Dec. 1998; Claussen et al. U.S. Pat. No. 5,158,916 issued 27 Oct. 1992; Claussen et al. U.S. Pat. No. 4,908,171 issued 13 Mar. 1990.

Claussen et al., "Squeeze Cast $\beta$—$Si_3N_4$—Al Composites," disclose mechanical pressure-assisted infiltration (referred to by Claussen et al. as "squeeze casting") of a conventional aluminum alloy into a porous reaction-bonded silicon nitride ($Si_3N_4$) preform to produce a $\beta$—$Si_3N_4$—Al composite exhibiting excellent mechanical properties. Travitzky et al., "Microstructure and Properties of Metal Infiltrated RBSN Composites," disclose gaseous pressure-assisted infiltration of RBSN with one of four different metallic materials—viz., aluminum (Al), aluminum alloy (Al—Mg—Si—Zn), titanium-aluminum (Ti—Al) intermetallic, and silicon (Si)—thus producing four different RBSN-metal composites.

Claussen et al., "Squeeze Cast $\beta$—$Si_3N_4$—Al Composites," prepared aluminum-silicon nitride composites, measured flexural strengths, and found that flexural strength was dramatically increased by infiltration of $Si_3N_4$ with Al. The present invention as often practiced provides for infiltration, into a reaction-bonded ceramic preform such as an RBSN preform, of one or more non-ceramic materials other than metal, such as polymeric materials or glass materials. It is believed by the present inventor that the inventive infiltration of such non-metallic materials into reaction-bonded ceramic preforms will yield increases in flexural strength similar to those reported by Claussen et al., "Squeeze Cast $\beta$—$Si_3N_4$—Al Composites."

The present invention's infiltration of a reaction-bonded ceramic preform can be accomplished in various ways, generally falling in either of two categories, namely, pressure (pressure-assisted) infiltration or pressureless infiltration. Pressureless infiltration involves no auxiliary application of pressure to an infiltrant that contacts a porous body; that is, pressureless infiltration relies entirely upon gravity and/or capillary action of the infiltrant to infiltrate the pores. "Melt" infiltration involves infiltration of a melted material, i.e., a solid material that has been heated up to melting temperature. Pressure-assisted infiltration can be of a mechanical pressure variety (wherein infiltrative force is applied by mechanical means, such as involving a piston-and-cylinder-like mechanism) or a gaseous pressure variety (wherein infiltrative force is applied by means of a vacuum, e.g., atmospheric pressure, created by a gas). By way of example, to make a metal-infiltrated or a polymer-infiltrated or a glass-infiltrated RBSN preform composite, the impregnation of RBSN by a metal can be performed via either pressure-assisted "melt" infiltration or pressureless "melt" infiltration of a metallic (metal or metal alloy) material or a polymeric material or a glass material, as the case may be. As another example, it may be appropriate to impregnate RBSN with a thermoset polymer via vacuum-assisted infiltration.

The inventive practitioner's choice of infiltrant or infiltrants can be based on consideration of criteria including ballistic performance, cost, and weight. Such consideration may involve balancing of these (and perhaps other) factors in terms of benefits and risks/detriments, particularly in view of the contemplated application(s). Inventive design specifications will vary in accordance with the threats to be protected against. The design requirements pertaining to ballistic performance, for instance, will depend on the nature of the threat. Penetration-resistance may be described as a "hard armor" attribute, whereas energy-absorption and damage-tolerance may be described as "soft armor" attributes.

To defend against projectiles at higher velocities, harder/firmer/more rigid infiltrants may afford better performance insofar as being more penetration-resistant. To defend against projectiles at lower velocities, softer/more flexible/more elastic infiltrants may afford better performance insofar as being more energy-absorptive and/or more damage-tolerant. Generally speaking, glass infiltrants will offer more penetration-resistance because of their greater hardness, whereas metal infiltrants or polymer infiltrants will offer more energy-absorption and damage-tolerance because of their more compliant properties. Notwithstanding these and other general characteristics of materials, the inventive practitioner will usually need to evaluate these and other design parameters in more specific terms.

Selection of the optimal infiltrant(s) will also depend on other factors, such as the properties of the ceramic, and the volume fraction of the infiltrant(s), e.g., infiltrant percentage versus ceramic percentage. Polymers are lighter than metals and are cheaper, but are softer. Metals with low melting temperatures and low density, such as aluminum, are generally preferable in terms of processing convenience; in particular, reducing the processing temperature will reduce undesirable chemical interactions with the ceramic, and will reduce processing costs. Silicon, for example, is chemically compatible with silicon nitride, and offers higher hardness and modulus than aluminum; however, silicon requires higher processing temperatures and also has a higher density (which represents a disadvantage for personal/personnel armor). On the other hand, material density (specific gravity) is usually not the final determination in an armor application, as the areal density of the armor construction needed to stop a specific threat is the real value of interest. A material with greater ballistic efficiency but also higher density may nevertheless prove to be propitious in an armor construction that is characterized by low areal density. The terms "areal density" and "areal packing density," as used synonymously herein, denote mass per unit area, such as measured in the geometric plane (straight or curved) of the front surface of an inventive composite armor plate.

The following U.S. patents, each of which is incorporated herein by reference, disclose body armor plates and helmets, and armor/protective systems involving same: Olson et al., U.S. Pat. No. 7,210,390 B1, issued 1 May 2007, entitled "Buoyance Device for Personnel Protective Plates"; Crye et al., U.S. Pat. No. 6,892,392 B2, issued 17 May 2005, entitled "Personal Body Armor"; Crye et al., U.S. Pat. No. 6,804,829 B2, issued 19 Oct. 2004, entitled "Advanced Combat Helmet System"; Crye et al., U.S. Pat. No. 7,237,270 B2, issued 3 Jul. 2007, entitled "Removable Garment Protective Assembly"; Crye et al., U.S. Pat. No. D569,043 S, issued 13 May 2008, entitled "Ballistic Armor Back Plate"; Crye et al., U.S. Pat. No. D569,044 S, issued 13 May 2008, entitled "Ballistic Body Armor Plate"; Crye et al., U.S. Pat. No. D569,045 S, issued 13 May 2008, entitled "Ballistic Body Armor Plate"; Crye et al., U.S. Pat. No. D569,046 S, issued 13 May 2008, entitled "Ballistic Body Armor Plate"; Crye et al., U.S. Pat. No. D573,311 S, issued 15 Jul. 2008, entitled "Ballistic Body Armor Plate."

Still referring to FIG. 1, and also referring to FIG. 2 through FIG. 13, the present invention provides multifarious embodiments of ballistic armor components includable in body armor (e.g., protective vest) systems or head armor (helmet) systems, such as would be suitable for wear by military or law enforcement personnel. The inventive body armor plates illustrated herein, which are illustrated by way of example, are characterized by double curvature and uniform (or approximately uniform) thickness. An inventive body armor plate may be useful, for instance, as a "small arms protective insert" ("SAPI"), to be inserted in a tactical vest. Various manners of utilizing inventive body armor plates will be apparent to the skilled artisan who reads the instant disclosure.

The geometric shapes depicted in FIG. 1 through FIG. 13 herein are merely exemplary of diverse geometric shapes that are possible for inventive practice of non-ceramic-infiltrated reaction-bonded-ceramic composite armor devices. Inventive configurations of diverse types, characterized by rectilinearity and/or curvilinearity, are possible. Body armor plate geometries are usually designed with bodily comfort, conformance, and freedom of motion in mind, in addition to ballistic considerations. Of interest in this regard are various geometric shapes of body armor plates disclosed by Crye et al. at the aforesaid U.S. Pat. Nos. 6,892,392, D569,043, D569,044, D569,045, D569,046, and D573,311.

EXAMPLE 1

Glass-Infiltrated RBSN Composite Body Armor Plates

The inventive composite armor devices 300 depicted in FIG. 2 through FIG. 5 are inventive composite armor devices 300 of the homogeneously infiltrated kind. Inventive body armor plate $300_{P1}$ (shown in FIG. 2 through FIG. 4) and inventive body armor plate $300_{P1X}$ (shown in FIG. 5) each include an RBSN preform phase 210 and a glass infiltrant phase 390. Glass infiltrant phase 390 at least substantially occupies the interstices (pores) defined by RBSN preform phase 210. The difference between inventive body armor plate $300_{P1}$ and inventive body armor plate $300_{P1X}$ is glass infiltrant material coating 370, present in the latter.

Figure 2:
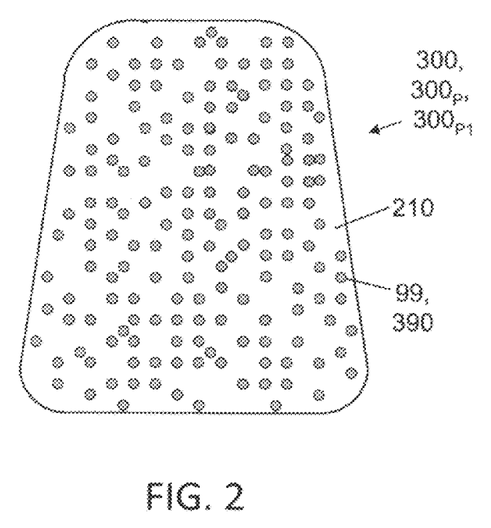
FIG. 2 is front plan view of a single-infiltrant embodiment of a body armor plate in accordance with the present invention.
Figure 3:
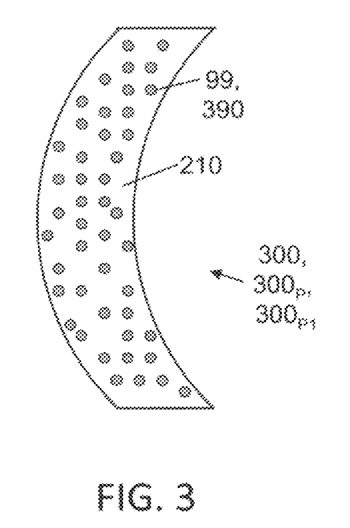
FIG. 3 is a side cross-sectional view of the inventive body armor plate shown in FIG. 2.
Figure 4:
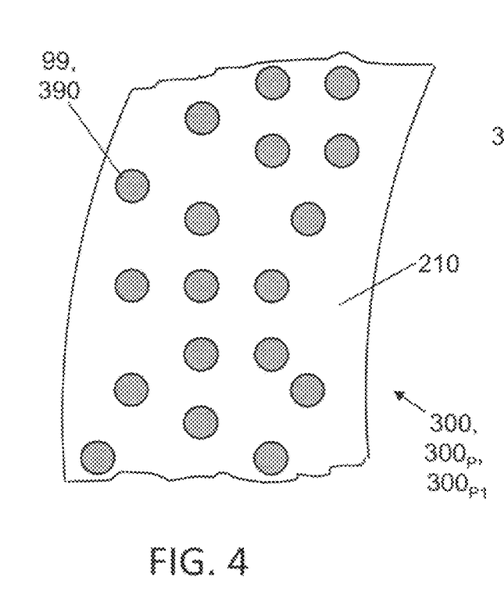
FIG. 4 is a partial and enlarged version of the view shown in FIG. 3.

The first (green body production) stage of fabrication of inventive body armor plate $300_{P1}$ or $300_{P1X}$ results in a porous silicon green body 100 having the same or approximately the same geometric shape as that shown in FIG. 2 and FIG. 3 of inventive body armor plate $300_{P1}$. The second (preform production) stage of inventive fabrication results in a porous RBSN preform 200 again having the same or approximately the same geometric shape. During the third (preform infiltration) stage of fabrication of inventive body armor plate $300_{P1}$ or $300_{P1X}$, glass material 390 is fired to the temperature at which it melts and its viscosity is low enough to penetrate the porosity of RBSN preform 200. For instance, RBSN preform 200 can be covered with frit (e.g., granulated glass 390) or with a glass 390 plate, and then melted (fired to the appropriate temperature).

Figure 5:
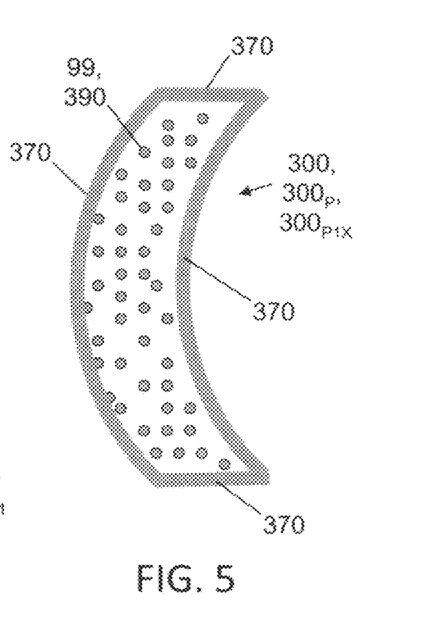
FIG. 5 is a side cross-sectional view of an inventive body army plate that is similar to the inventive body plate shown in FIG. 2 through FIG. 4, but that includes an exterior coating composed of the infiltrant material.

According to inventive embodiments of an exteriorly coated body armor plate $300_{P1X}$ such as illustrated in FIG. 5, an excessive amount of glass 390 can be infiltrated into RBSN preform 200 so that some excess glass 390 covers the outside of the infiltrated preform, thus providing an overglaze 370 (composed of glass infiltrant 390) when hardened. Glass coating 370 can be a complete glass coating (covering the entire outside surface of RBSN preform 200) or a partial glass coating (covering part of the outside surface of RBSN preform 200).

Generally speaking, the infiltration of a non-ceramic infiltrant material 390 into and through pores 99 of a reaction-bonded ceramic preform 200 can be controlled and/or encouraged in any one of, or any combination of, several ways including the following: (i) applying (and adjusting) pressure during infiltration; (2) applying (and adjusting) temperature (i.e., heat) during infiltration; (3) quantifying the infiltrant material to be infiltrated; (4) engineering the porosity (density) of the green body (i.e., the "green density"). If infiltrative-assistive pressure is applied during infiltration, this pressure can be mechanical pressure and/or gaseous pressure (e.g., vacuum pressure).

The porosity of the green body—in other words, its pore size—can be selected by controlling the size of the precursor particulate to be formed into the green body. Essentially, two physical properties of an infiltrant—namely, the infiltrant's surface tension and the infiltrant's viscosity—determine the ability of the infiltrant to infiltrate into and through the pores of a ceramic preform. The second (preform production) stage of inventive fabrication also presents an opportunity to affect the porosity of the green body based on the "conversion kinetics," i.e., the kinetics of the conversion from precursor-constituted green body to ceramic-constituted preform. The conversion kinetics are determined by which gas (e.g., nitrogen) is being applied to the precursor material, and also by the temperature and pressure being brought to bear on the material conversion process.

The inventive principles and techniques described in the preceding two paragraphs are applicable to uni-regional (homogeneous) inventive practice as well as plural-regional (heterogeneous) inventive practice.

EXAMPLE 2

Glass-Polymer-Infiltrated RBSN Composite Body Armor Plates

FIG. 6 through FIG. 11 can be understood to be illustrative of an inventive double-layer configuration characterized by any one of the following combinations of dissimilar composite materials: glass-infiltrated RB ceramic and polymer-infiltrated RB ceramic; glass-infiltrated RB ceramic and metal-infiltrated RB ceramic; metal-infiltrated RB ceramic and polymer-infiltrated RB ceramic.

Let us assume that the inventive composite body armor device 300 depicted in FIG. 6 through FIG. 11 is an inventive double-layer composite body armor plate $300_{P2}$ having: (a) a glass-infiltrated RBSN layer 350A, with the glass phase 390A filling larger preform 200 pores 99; and, (b) a polymer-infiltrated (e.g., elastomer-infiltrated) RBSN layer 350B, with the polymer 390B filling smaller preform 200 pores 99. Although we are proceeding on this assumption by way of example, it is to be recognized that, alternatively, the inventive double-layer composite body armor plate $300_{P2}$ shown can be embodied so as to have the porosities reversed, with the glass filling the smaller pores and the polymer filling the larger pores.

The inventive composite armor devices 300 depicted in FIG. 6 through FIG. 10 are inventive composite armor devices 300 of the heterogeneously infiltrated kind. Similarly as shown in FIG. 2 through FIG. 5 regarding inventive homogeneously infiltrated composite armor devices $300_{P1}$ and $300_{P1X}$, inventive non-coated heterogeneously infiltrated body armor plate $300_{P2}$ (shown in FIG. 6 through FIG. 8) and inventive coated heterogeneously infiltrated body armor plate $300_{P2X}$ (shown in FIG. 9) each include an RBSN preform phase 210 and an overall infiltrant phase 390, which at least substantially occupies the interstices (pores) defined by RBSN preform phase 210.

In contrast to an inventive homogeneously infiltrated body armor plate $300_{P1}$, in an inventive heterogeneously infiltrated body armor plate $300_{P2}$ the overall infiltrant phase 390 consists of two disparate infiltrant phases—e.g., a glass-infiltrant phase 390A, and a polymer-infiltrant phase 390B. Glass-infiltration region 350A contains a first portion of RBSN preform phase 210, and glass infiltrant phase 390A. Polymer-infiltration region 350B contains a second portion of RBSN preform phase 210, and polymer infiltrant phase 390B.

Figure 6:
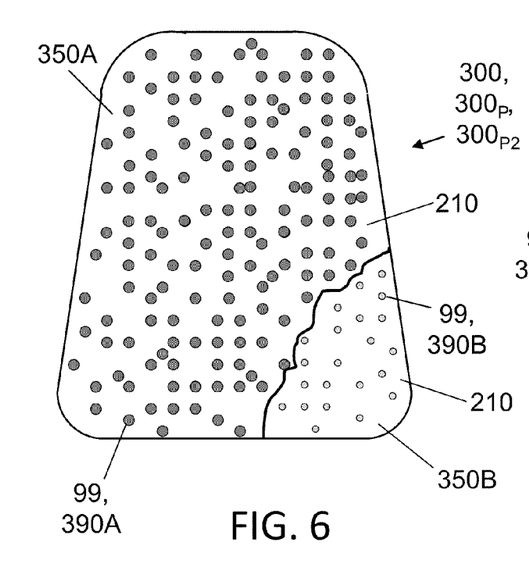
FIG. 6 is front plan view, with a portion removed to reveal some interior structure, of a double-infiltrant embodiment of a body armor plate in accordance with the present invention.
Figure 7:
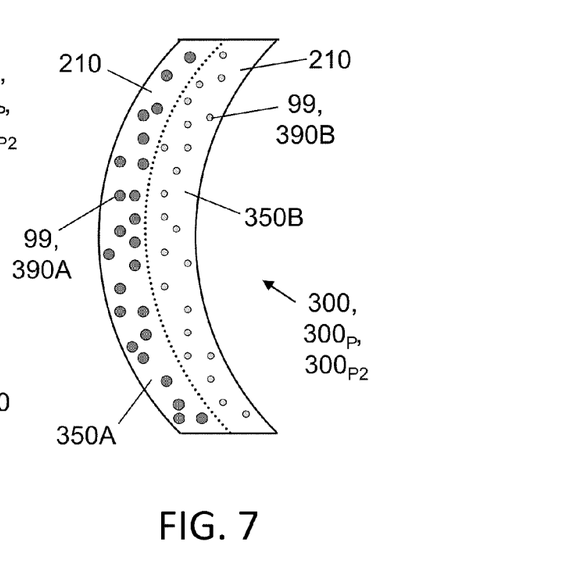
FIG. 7 is a side cross-sectional view of the inventive body armor plate shown in FIG. 6.
Figure 8:
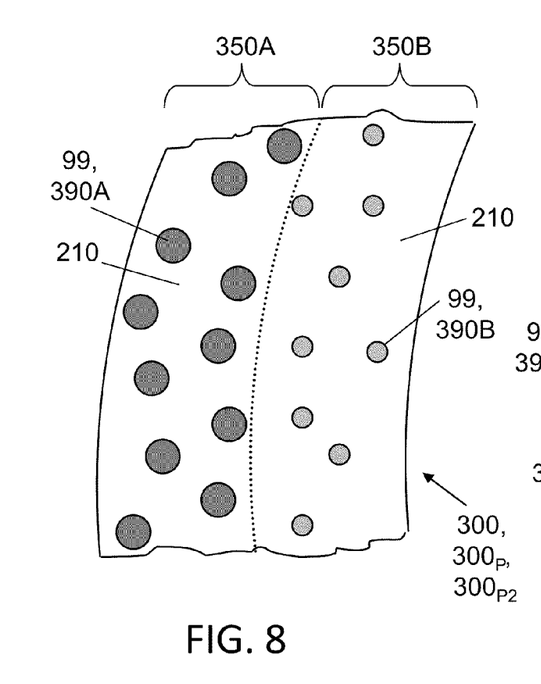
FIG. 8 is a partial and enlarged version of the view shown in FIG. 7.

Inventive glass-polymer composite body armor plate $300_{P2}$ is representative of a genre of inventive plural-infiltrant body/head armor devices 300 that combines "hard armor" and "soft armor" characteristics. For instance, according to typical hard-and-soft armor embodiments of the present invention's heterogeneously infiltrated body armor plate $300_{P2}$, two different infiltrants are selected so that the infiltrant intended to confront projectile impact is "hard," and the infiltrant intended to abut the human body or head is "soft." By way of example, a glass-infiltrated RBSN layer 350A can afford the hard armor component of inventive body armor plate $300_{P2}$, and a polymer-infiltrated (e.g., elastomer-infiltrated) RBSN layer 350B can afford the soft armor component of inventive body armor plate $300_{P2}$. The less forgiving glass-infiltrated RBSN region 350A constitutes the front ("strike") region of the inventive armor plate. The more forgiving polymer-infiltrated RBSN region 350B, positioned adjacent to the wearer's body, constitutes the back ("cushioning") region of the inventive armor plate.

Figure 10:
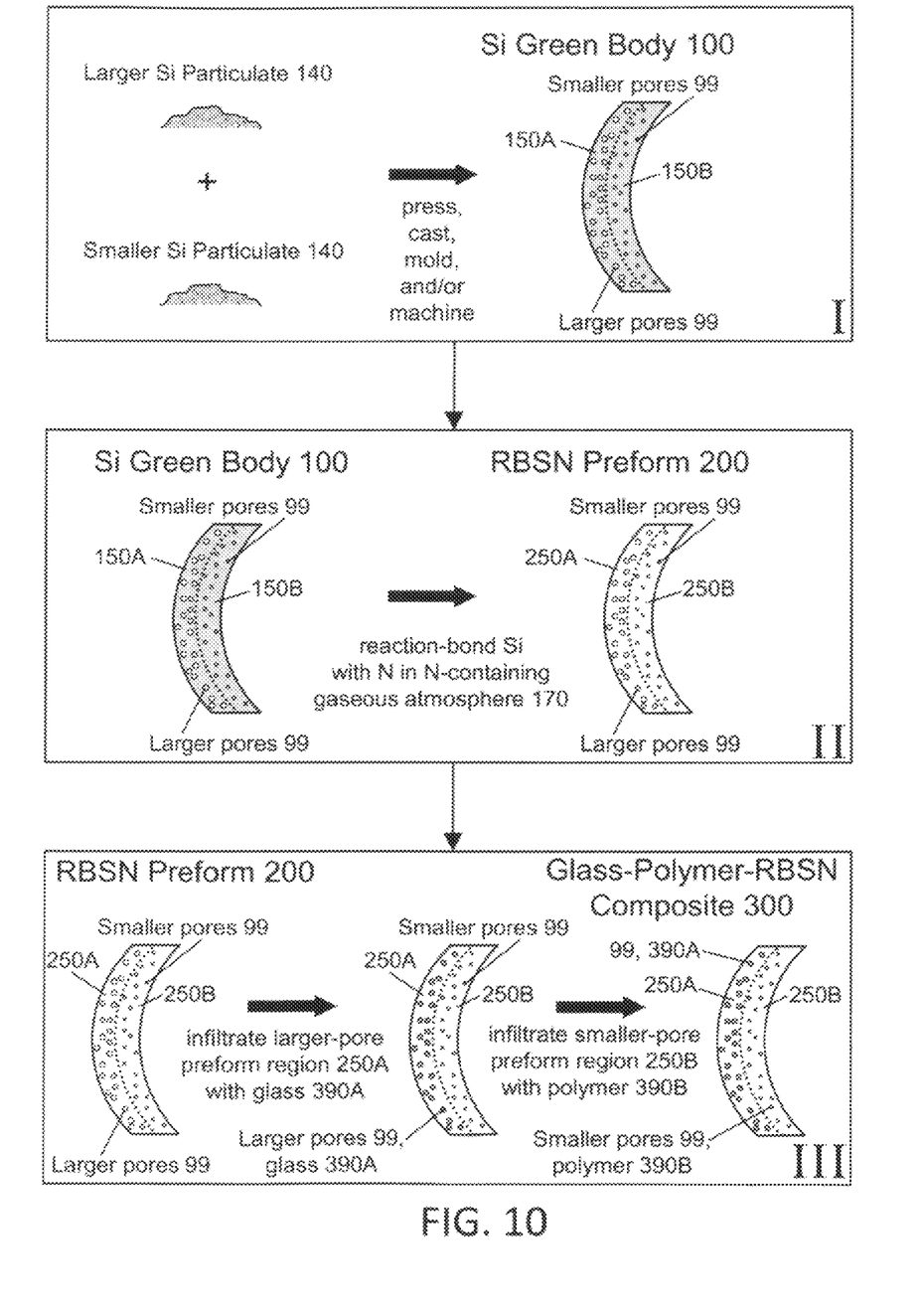

The primary distinction between inventive homogeneously infiltrated composite armor devices $300_{P1}$ and $300_{P1X}$, and heterogeneously infiltrated composite armor devices $300_{P2}$ and $300_{P2X}$, is that the former are each infiltrated with one non-ceramic infiltrant material 390, whereas the latter are each infiltrated with two non-ceramic infiltrant materials 390. With respect to making an inventive homogeneously infiltrated composite device/article 300 versus making an inventive heterogeneously infiltrated composite device/article 300, generally the principal differences will reside in the first stage and/or third stage of inventive fabrication. As illustrated in FIG. 10, one or more useful techniques are carried out in accordance with typical practice of the present invention, in order to make an inventive heterogeneously infiltrated composite device/article 300.

Inventive porosity-engineering technique can be practiced during the first (green body production) stage of fabrication of an inventive plural-infiltration composite device/article 300 such as inventive double-infiltration body armor plate $300_{P2}$ shown in FIG. 6 through FIG. 10. The goal according to this inventive technique is to "engineer" the pore 99 structure of the green body 100; more specifically, the objective is to create at least two distinct regions 150 of porous green body 100, each region 150 having a different pore 99 size. The size of the powder precursor particles 140 will determine the size of the pores 99 of the green body 100. The pressing/casting/molding of the green body 100 can be performed so that a first region contains larger powder precursor particles 140, and a second region contains smaller powder precursor particles 140. In essence, the plural porosity regions 150 of unequal pore 99 size represent a "porosity gradient" characterizing green body 100—i.e., a gradient in the pore 99 structure of the green body 100.

In the case, for instance, of making an inventive double-infiltrant composite body armor device 200 such as shown in FIG. 6 through FIG. 10, a larger-pore green body region 150A and a smaller-pore green body region 150B are generated by using: larger silicon powder granules/particulate 140 to produce the larger-pore region 150A; smaller silicon powder granules/particulate 140 to produce smaller-pore region 150B. The resultant green body 100, configured to become an inventive body armor plate 300 after further processing, has two regions 150 that may be described as "layers," due to the generally "flat" (straight or curved) geometry of inventive body armor plate 300—namely, larger-pore green body layer (region) 150A and smaller-pore green body layer (region) 150B.

In addition or alternative to particulate size selection in the first stage, conversion kinetics can controllably be brought to bear in the second stage so as to bring about differences in porosity between layers 250A and 250B of preform 200. For instance, during the reaction-bonding conversion process, the inventive practitioner can apply, on two opposite sides of green body 100, different temperatures and/or pressures and/or nitrogen-inclusive atmospheres, thereby dichotomizing the preform 200 to which the green body 100 is being converted. Here again, the aim is an RB ceramic preform 200 having two different layers 250A and 250B of differing porosities.

Upon completion of the second (preform production) stage of inventive fabrication, the resultant porous RBSN preform 200 is characterized by two preform layers (regions) 250, viz., preform region 250A (having larger pores 99) and preform region 250B (having smaller pores). During the third (preform infiltration) stage of fabrication of inventive body armor plate 300$_{P2}$ or 300$_{P2X}$, glass material 390A is fired to a melting temperature at which its viscosity is sufficiently low to penetrate the porosity of RBSN preform region 250A. Separately, polymeric material 390B is fired to a melting temperature at which its viscosity is sufficiently low to penetrate the porosity of RBSN preform region 250B.

Glass material 390A and polymeric material 390B will normally be infiltrated into their corresponding preform regions 250 at different times; in this manner, the infiltration to be performed first in time with be shepherded by the porosity of the corresponding preform region 250. For instance, glass 390A can be infiltrated into preform region 250A so that the glass 390 physically ceases to be conveyed beyond the interface 50 between preform regions 250A and 250B. The interface 50 acts, in a sense, as a barrier to further transmission, since the unsuitably porous preform region 250B is not an effective transmission medium for glass 390A.

When different pore sizes are inventively engineered, this will frequently be accompanied by different pore volume fractions. Accordingly, inventive porosity engineering is useful not only for achieving different pore sizes in different regions of the inventive structure, but—additionally or alternatively—for achieving different pore volume fractions in different regions of the inventive structure. The porosity size differentiation may be motivated to promote different infiltrative abilities in different regions, whereas the porosity volume fraction differentiation may be motivated to promote different material properties in different regions.

Figure 11:
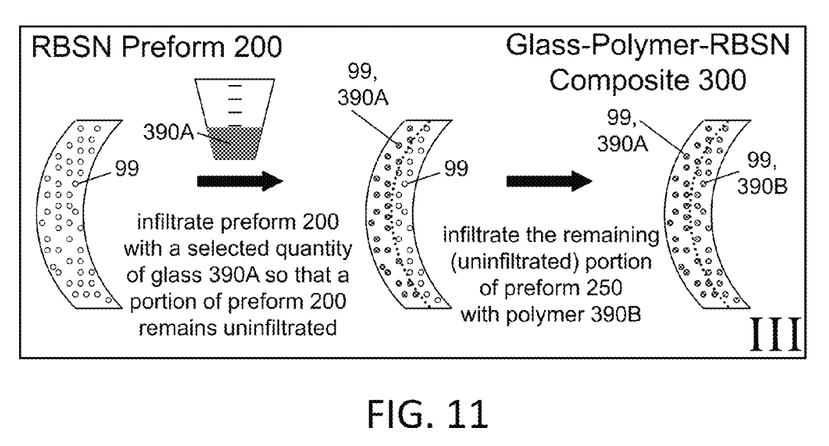
FIG. 11 is a schematic, similar to the lowest box shown in FIG. 1 or the lowest box shown in FIG. 10, illustrating an inventive "quantified infiltrant" technique, which can be practiced in inventively fabricating an inventive plural-infiltrant embodiment.

The inventive technique of quantification of infiltrant can be performed either together with, or in absence of, the inventive technique of gradation (e.g., stratification) of pores. As illustrated in FIG. 11, a selected quantity of infiltrant can be caused to contact the desired area of the preform 250. For instance, a specific amount of glass infiltrant 390A, for instance in frit form or plate form, can be poured or placed onto the exposed surface/side of preform region 250A, prior to heating the glass infiltrant 390A to an appropriate melting temperature for infiltrating the pores 99 of preform 250. Prior to heating, the exact amount of glass infiltrant 390A is calculated so that, when completely infiltrating preform 250, the glass infiltrant 390A will partially infiltrate the preform 250 to a desired extent. In other words, the glass infiltrant 390A will infiltrate preform region 250A, and the combination will be permitted to cool and solidify so that a partially completed ceramic composite device 300 includes a glass-infiltrated ceramic-preform region 350A and a non-infiltrated preform region 250B. Subsequent to the solidification of glass infiltrant 390A and the concomitant formation of glass-infiltrated ceramic-preform region 350A, preform region 250B is infiltrated with polymer infiltrant 390B, thereby forming polymer-infiltrated ceramic-preform region 350B.

The volumetric proportions of the different non-ceramic-infiltrated RB-ceramic-preform regions 350A, 350B, etc., can vary in inventive practice, depending on the inventive embodiment. For instance, the glass-infiltrated ceramic-preform region 350A and the polymer-infiltrated ceramic-preform region 350B are shown to be approximately equal in volume; in other words, in terms of percentages, the glass-polymer-infiltrated RBSN-preform plate 300$_{P2}$ is 50-50, or approximately so. The skilled artisan reading this disclosure will appreciate that practically any volumetric proportions of the plural non-ceramic-infiltrated RB-ceramic-preform regions of an inventive plural-infiltrated device/article are possible in inventive practice.

Figure 9:
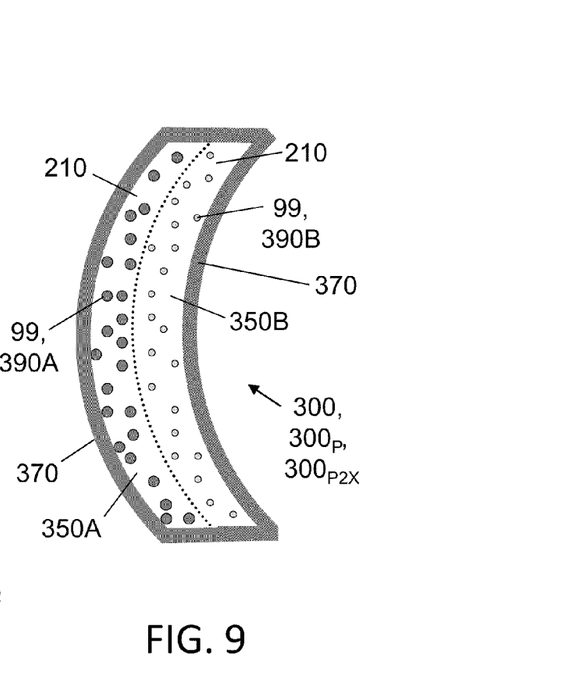
FIG. 9 is a side cross-sectional view of an inventive body army plate that is similar to the inventive body plate shown in FIG. 6 through FIG. 8, but that includes an exterior coating composed of the infiltrant material.

According to inventive plural-infiltrant embodiments such as illustrated in FIG. 9, an excessive amount of one, some or all infiltrants 390 are infiltrated into an RB-ceramic preform 200 so that some excess infiltrant(s) 390 cover(s) the outside, or part of the outside, of the infiltrated RB-ceramic preform, thus providing a coating or partial coating 370 when hardened. For instance, as distinguished from inventive non-coated heterogeneously infiltrated body armor plate 300$_{P2}$, a complete or partial glass infiltrant material coating 370A (adjacent to glass-infiltration region 350A) and a complete or partial polymer infiltrant-material coating 370B (adjacent to polymer-infiltration region 350B) are additionally included in inventive heterogeneously infiltrated body armor plate 300$_{P2X}$.

Alternatively, the coating 370 can be rendered so as to include, for instance: (i) a complete or partial glass infiltrant-material coating 370A adjacent to glass-infiltration region 350A, but no polymer infiltrant-material coating 370B; or, (ii) a complete or partial polymer infiltrant-material coating 370B adjacent to polymer-infiltration region 350B, but no glass infiltrant material coating 370A; or, (iii) a complete or partial glass infiltrant material coating 370A adjacent to glass-infiltration region 350A and polymer-infiltration region 350B, but no polymer infiltrant-material coating 370B; or, (ii) a complete or partial polymer infiltrant-material coating 370B adjacent to glass-infiltration region 350A and polymer-infiltration region 350B, but no glass infiltrant-material coating 370A.

EXAMPLE 3

Glass-Metal-Polymer-Infiltrated RBSN Composite Body Armor Plates

Figure 12:
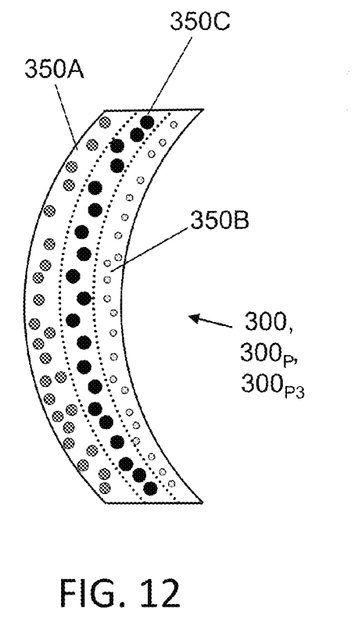
FIG. 12 is a side cross-sectional view of a triple-infiltrant embodiment of a body armor plate in accordance with the present invention.

Inventive plural-infiltrant body armor plates $300_{P2}$ (shown, by way of example, in FIG. 6 through FIG. 11) are of the inventive double-infiltrant variety. In contrast, exemplary inventive plural-infiltrant body armor plate $300_{P3}$, shown in FIG. 12, is of the inventive triple-infiltrant variety. Glass-metal-polymer-Infiltrated RBSN composite body armor plate 300 includes a glass-infiltration region 350A, a metal-infiltration (e.g., aluminum-infiltration, steel-infiltration, or titanium-infiltration) region 350C, and a polymer-infiltration (e.g., elastomer-infiltration) region 350B. The three regions of the generally flat-shaped inventive body armor plate $300_{P3}$ are aptly described as "layers." In the inventive triple-layer body armor plate $300_{P3}$, glass-infiltration layer (region) 350A and polymer-infiltration layer (region) 350B "sandwich" therebetween the metal-infiltration layers (region) 350C.

A decreasingly "hard" quality of the inventive ballistic armor system $300_{P3}$ is associated with its adjacently layered configuration of: (a) hardest: glass-infiltrated RBSN front ("strike") region 350A; then, (b) softer: metal-infiltrated RBSN "intermediate" region 350C; then, (c) softest: polymer-infiltrated RBSN back ("cushioning") region 350B. Glass-infiltration region 350A is primarily penetration-resistive, and secondarily damage-tolerant and/or energy-absorptive. Metal-infiltration region 350C is primarily damage-tolerant, and secondarily energy-absorptive. Polymer-infiltration region 350B is primarily energy-absorptive, and secondarily damage-tolerant.

EXAMPLE 4

Glass-Polymer-Infiltrated RBSN Composite Helmets

Figure 13:
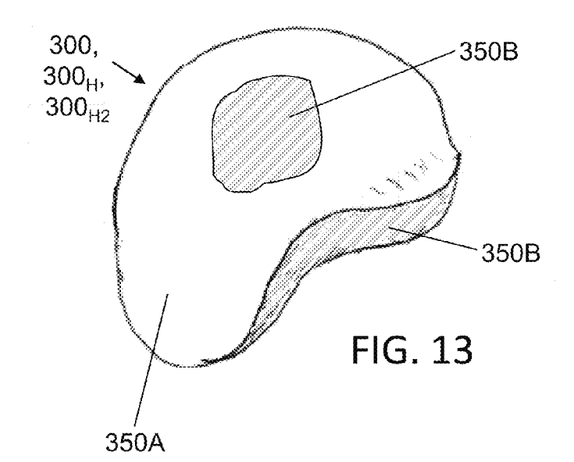
FIG. 13 is a perspective view, with a portion removed to reveal some interior structure, of a double-infiltrant embodiment of a helmet in accordance with the present invention.

The inventive hard armor/soft armor configurations exemplified in FIG. 6 through FIG. 12 can similarly be embodied in an inventive plural-infiltrant helmet $300_{H2}$ such as shown in FIG. 13. As shown in FIG. 13 the less forgiving glass-infiltrated RBSN region 350A constitutes the outside ("strike") region of the inventive armor helmet $300_{H2}$; the more forgiving polymer-infiltrated (e.g., elastomer-infiltrated) RBSN region 350B, positioned adjacent to the wearer's head, constitutes the inside ("cushioning") region of the inventive armor helmet $300_H$. An inventive helmet $300_H$ can also be embodied as a single-infiltrant helmet (not shown), which can include, for instance, a glass infiltrant if "hard" helmet characteristics are desired, or a polymeric (e.g., elastomeric) infiltrant if "soft" helmet characteristics are desired. As another alternative, an inventive helmet $300_H$ can be embodied as a triple-infiltrant helmet (not shown) along the lines of triple-infiltrant body armor plate $300_{P3}$ shown in FIG. 12.

EXAMPLE 5

Lubricant-Infiltrated RBSN Composite Rolling Elements for Roller Bearings

The present invention can be practiced to prevent or mitigate wear in mechanical applications. For instance, with reference to FIG. 14, inventive lubricant-infiltrated RBSN composite bearing ball $300_W$ includes a lubricious infiltrant such as graphite or a fluoropolymer. The inventive composite bearing ball $300_W$ acts, in effect, as a self-lubricating rolling element in a roller bearing. A sufficiently great percentage (in the range between approximately 70% and approximately 80%) of the volume of the inventive composite bearing ball $300_W$ is RBSN material 210 for structural integrity and durability, while a sufficiently great percentage of its volume is lubricant-infiltrant 210 for wear amelioration. During operation of the ball bearing, small amounts of lubricant-infiltrant $390_{LUB}$ are continually released from inventive composite bearing ball $300_W$ so that some lubricant-infiltrant $390_{LUB}$ remains in a state of liquification on the outside surface of the inventive ball $300_W$, thus constantly acting as a slippery coating.

Figure 14:
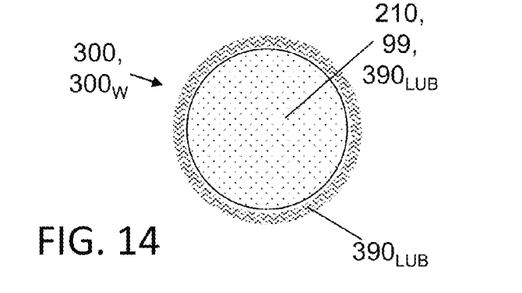
FIG. 14 is a cross-sectional view of an embodiment of a self-lubricating ball bearing composite, characterized by a seeping lubricious infiltrant phase, in accordance with the present invention.

FIG. 14 is illustrative of an embodiment of a inventive rolling component. The present invention lends itself to many other mechanical wear-type applications, such as involving non-rolling components. For instance, an inventive composite $300_W$ can be embodied as a race, a sleeve bearing, or a compressor cylinder liner. Inventive practice is possible for practically any application involving relatively sliding surfaces.

EXAMPLE 6

Bio-Agent-Infiltrated RBSN Composite Medical Devices

For medical applications, an inventive device can include a porous reaction-bonded ceramic material and a non-ceramic infiltrant (e.g., polymeric) that is a biologically active agent or that is biodegradable. For instance, an inventive medical device can be implanted in a person's body, and have an infiltrant that is a drug or other biofunctional material. The biologically active infiltrant is gradually released from the RB ceramic matrix and thus delivered inside the person's body by the inventive medical device. As another example, an inventive medical device can be surgically (orthopedically) placed in a person's joint, e.g., knee or elbow. The inventive medical device's infiltrant is a biodegradable material that gradually degrades (e.g., dissolves), thereby exposing the porosity of the RB ceramic matrix and permitting ingrowth of bone.

The following U.S. patents, each of which is incorporated herein by reference, are of interest in the medical realm: Tormala et al. U.S. Pat. No. 7,419,681 B2 issued 2 Sep. 2008; Lye et al. U.S. Pat. No. 7,294,409 B2 issued 13 Nov. 2007; Greenberg U.S. Pat. No. 7,181,287 B2 issued 20 Feb. 2007; Lee et al. U.S. Pat. No. 6,972,130 B1 issued 6 Dec. 2005; Mochizuki et al. U.S. Pat. No. 6,737,493 B2 issued 18 May 2004; Tormala et al. U.S. Pat. No. 6,579,533 B1 issued 17 Jun. 2003; Agrawal et al. U.S. Pat. No. 5,947,893 issued 7 Sep. 1999; Agrawal et al. U.S. Pat. No. 5,876,446 issued 2 Mar. 1999; Rizzo U.S. Pat. No. 5,141,748 issued 25 Aug. 1992.

Merely a few inventive examples are described herein, but they convey the present invention's comprehensive potentiality based on variation of inventive configurations and/or constituents. As previously discussed herein, numerous inventive variations in configurations and/or preform materials and/or infiltrant materials are possible, as are their associated functions and purposes. The skilled artisan who reads the instant disclosure will appreciate the diverse possibilities of inventive practice, including in the following respects: (i) any of various reactive powders, silicon or otherwise, may be suitable for being shaped to form a green body; (ii) any of various substances, nitrogen or otherwise, may be suitable for being reaction-bonded with a green body to form a reaction-bonded ceramic preform; (iii) any of various reaction-bonded ceramic preforms, RSBN or otherwise, may be suitable for being infiltrated by a non-ceramic material to form a non-ceramic infiltrated reaction-bonded preform composite material; (iv) any of, or any combination of, various non-ceramic infiltrants may be suitable for infiltrating a non-ceramic material to form a non-ceramic infiltrated reaction-bonded preform composite material; (v) any of various shapes can be obtained of a green body, and hence of the associated reaction-bonded ceramic preform, and hence of the associated non-ceramic-infiltrated reaction-bonded preform composite material.

The present invention, which is disclosed herein, is not to be limited by the embodiments described or illustrated herein, which are given by way of example and not of limitation. Other embodiments of the present invention will be apparent to those skilled in the art from consideration of the instant disclosure, or from practice of the present invention. Various omissions, modifications and changes to the principles disclosed herein may be made by one skilled in the art without departing from the true scope and spirit of the present invention, which is indicated by the following claims.

What is claimed is:

1. A composite structure comprising a reaction-bonded ceramic preform and at least two different non-ceramic infiltrants, at least one said non-ceramic infiltrant being glass, at least one said non-ceramic infiltrant being polymer, said reaction-bonded ceramic preform being characterized by porosity in the approximate range between ten percent and sixty percent of its volume, each said non-ceramic infiltrant filling at least one portion of said porosity, said at least two non-ceramic infiltrants at least substantially filling said porosity, wherein:
    said composite structure is characterized by plural regions;
    each said region corresponds to a said portion of said porosity and has a said non-ceramic infiltrant;
    at least a first said region has a glass said non-ceramic infiltrant and corresponds to a said portion of said porosity that is characterized by a first pore size;
    at least a second said region has a polymer said non-ceramic infiltrant and corresponds to a said portion of said porosity that is characterized by a second pore size that differs from said first pore size.

2. A composite structure comprising a reaction-bonded ceramic preform and at least two different non-ceramic infiltrants, at least one said non-ceramic infiltrant being glass, at least one said non-ceramic infiltrant being polymer, said reaction-bonded ceramic preform being characterized by porosity in the approximate range between ten percent and sixty percent of its volume, each said non-ceramic infiltrant filling at least one portion of said porosity, said at least two non-ceramic infiltrants at least substantially filling said porosity, wherein:
    said composite structure is characterized by plural regions;
    each said region corresponds to a said portion of said porosity and has a said non-ceramic infiltrant;
    at least a first said region has a glass said non-ceramic infiltrant and corresponds to a said portion of said porosity that is characterized by a first pore size;
    at least a second said region has a polymer said non-ceramic infiltrant and corresponds to a said portion of said porosity that is characterized by a second pore size;
    at least a third said region has a third said non-ceramic infiltrant and corresponds to a said portion of said porosity that is characterized by a third pore size;
    the third said non-ceramic infiltrant is selected from the group consisting of glass said non-ceramic infiltrant and polymer said non-ceramic infiltrant.

3. A composite structure comprising a reaction-bonded ceramic preform and at least two different non-ceramic infiltrants, at least one said non-ceramic infiltrant being glass, at least one said non-ceramic infiltrant being polymer, said reaction-bonded ceramic preform being characterized by porosity in the approximate range between ten percent and sixty percent of its volume, each said non-ceramic infiltrant filling at least one portion of said porosity, said at least two non-ceramic infiltrants at least substantially filling said porosity, said composite structure being characterized by plural regions, each said region corresponding to a said portion of said porosity and having a said non-ceramic infiltrant, wherein a first said region corresponds to a said portion of said porosity that is characterized by a first pore size, and wherein a second said region corresponds to a said portion of said porosity that is characterized by a second pore size that differs from said first pore size.

4. The composite structure of claim 3, wherein a third said region corresponds to a said portion of said porosity that is characterized by a third pore size that differs from said first pore size and said second pore size.

* * * * *